(12) United States Patent
Kondo et al.

(10) Patent No.: US 7,220,548 B2
(45) Date of Patent: *May 22, 2007

(54) PARTIAL HOMOLOGOUS RECOMBINATION OF DNA CHAIN

(75) Inventors: Kazuhiro Kondo, Chiba (JP); Michio Oishi, Chiba (JP); Osamu Ohara, Chiba (JP)

(73) Assignees: Aisin Cosmos R&D Co., Ltd., Chiba (JP); Kazusa DNA Research Institute Foundation, Chiba (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/798,750

(22) Filed: Mar. 10, 2004

(65) Prior Publication Data

US 2004/0180374 A1    Sep. 16, 2004

(30) Foreign Application Priority Data

Mar. 13, 2003    (JP)    ............................. 2003-068176

(51) Int. Cl.
*C12Q 1/68*    (2006.01)
(52) U.S. Cl. ......................................................... 435/6
(58) Field of Classification Search ..................... None
See application file for complete search history.

(56) References Cited

U.S. PATENT DOCUMENTS

| | | | |
|---|---|---|---|
| 4,888,274 A | | 12/1989 | Radding et al. |
| 5,460,941 A | | 10/1995 | Camerini-Otero et al. |
| 5,707,811 A | | 1/1998 | Ferrin et al. |
| 5,834,252 A | * | 11/1998 | Stemmer et al. ........... 435/91.1 |
| 6,114,121 A | | 9/2000 | Fujiwara et al. |
| 6,613,522 B2 | * | 9/2003 | Kondo et al. .................. 435/6 |

OTHER PUBLICATIONS

Arnold et al., The Journal of Biological Chemistry 275(16):12261-12265 (2000).*
Bonaldo, M.F., et al., "Normalization and Subtraction: Two Approaches to Facilitate Gene Discovery," *Genome Research* 6(9):791-806, 1996.
Diatchenko, L., et al., "Suppression Subtractive Hybridization: A Versatile Method for Identifying Differentially Expressed Genes," *Methods Enzymology* 303:349-380, 1999.
"GeneTrapper® cDNA Positive Selection System," *Invitrogen Instruction Manual*, Cat. No. 10356-020, Life Technologies, Inc., Rockville, M.D., at least as early as 1997.
Hedrick, S.M., et al., "Isolation of cDNA Colones Encoding T Cell-Specific Membrane-Associated Proteins," *Nature* 308:149-153, 1984.
Liang, P., et al., "Analysis of Altered Gene Expression by Differential Display," *Methods in Enzymology* 254:304-321, 1995.

* cited by examiner

*Primary Examiner*—Mark L. Shibuya
*Assistant Examiner*—Jeffrey S. Lundgren
(74) *Attorney, Agent, or Firm*—Christensen O'Connor Johnson Kindness PLLC

(57) ABSTRACT

The present invention provides a method of constructing a circular DNA library having an increased content of a desired first dsDNA by removing a second dsDNA using RecA protein to introduce a target single strand nucleic acid by homologous recombination at the 3' terminal portion of the second dsDNA, whereby the target DNA has a 3' terminal portion that differs from the 3' terminal portion of the second dsDNA to prevent circularization, thereby creating a triple stranded DNA portion at the 3' terminal end of the second dsDNA, adding Exonuclease I to digest the displaced first strand of the second dsDNA, ligating the DNA fragments to circularize the desired first dsDNA, removing the linear second dsDNA, thereby constructing the circularized DNA library having an increased content of the desired first dsDNA.

6 Claims, 5 Drawing Sheets

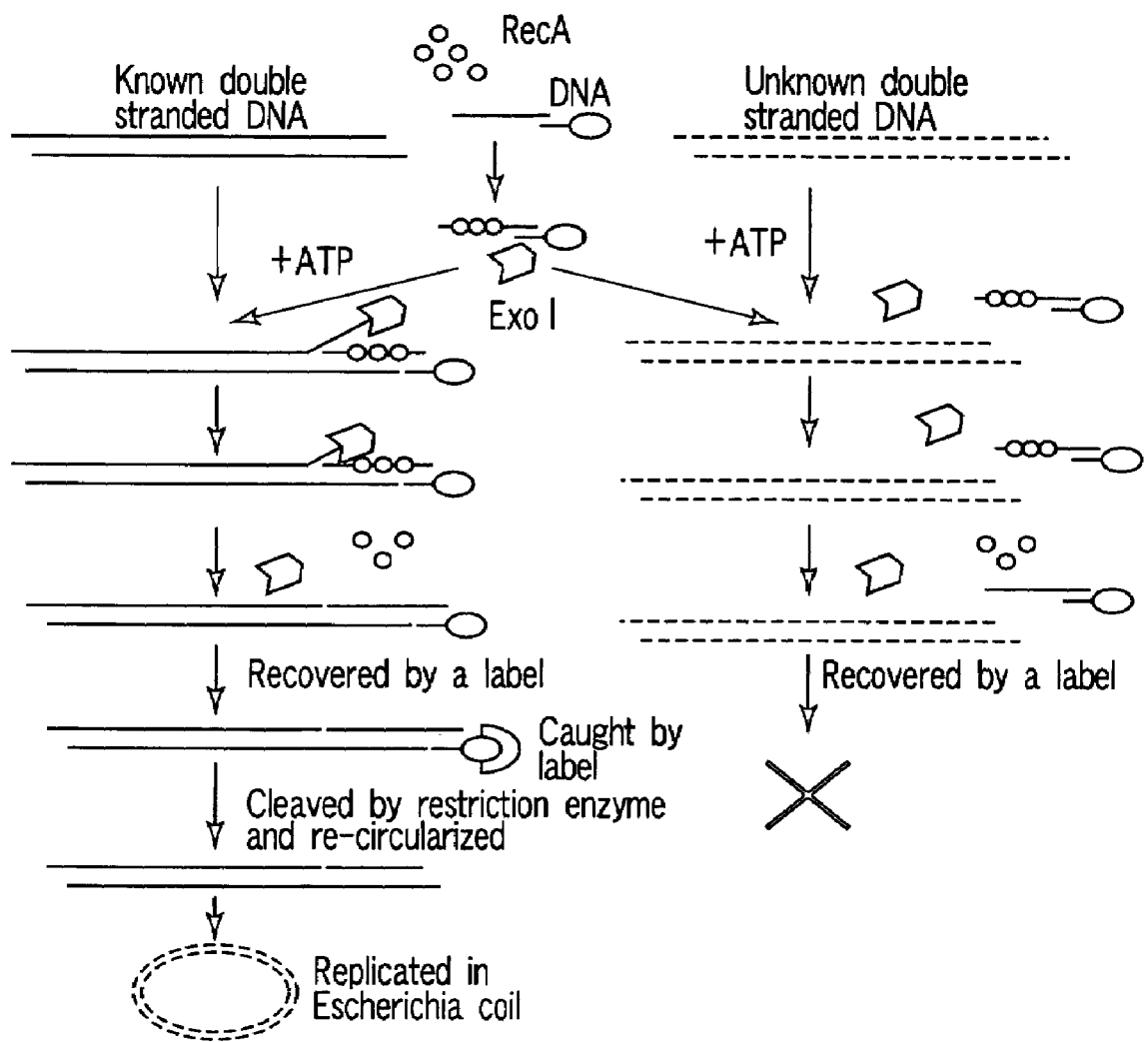
F I G. 3

1: Without removal treatment
2: Removal of plasmid with no insert

1: Without removal treatment
2: Removal of plasmid with no insert by RNA

1: Without RecA reaction after miniprep
2: With RecA reaction(25mer) after miniprep
3: With RecA reaction(30mer) after miniprep
4: With RecA reaction(40mer) after miniprep
5: With RecA reaction(60mer) after miniprep

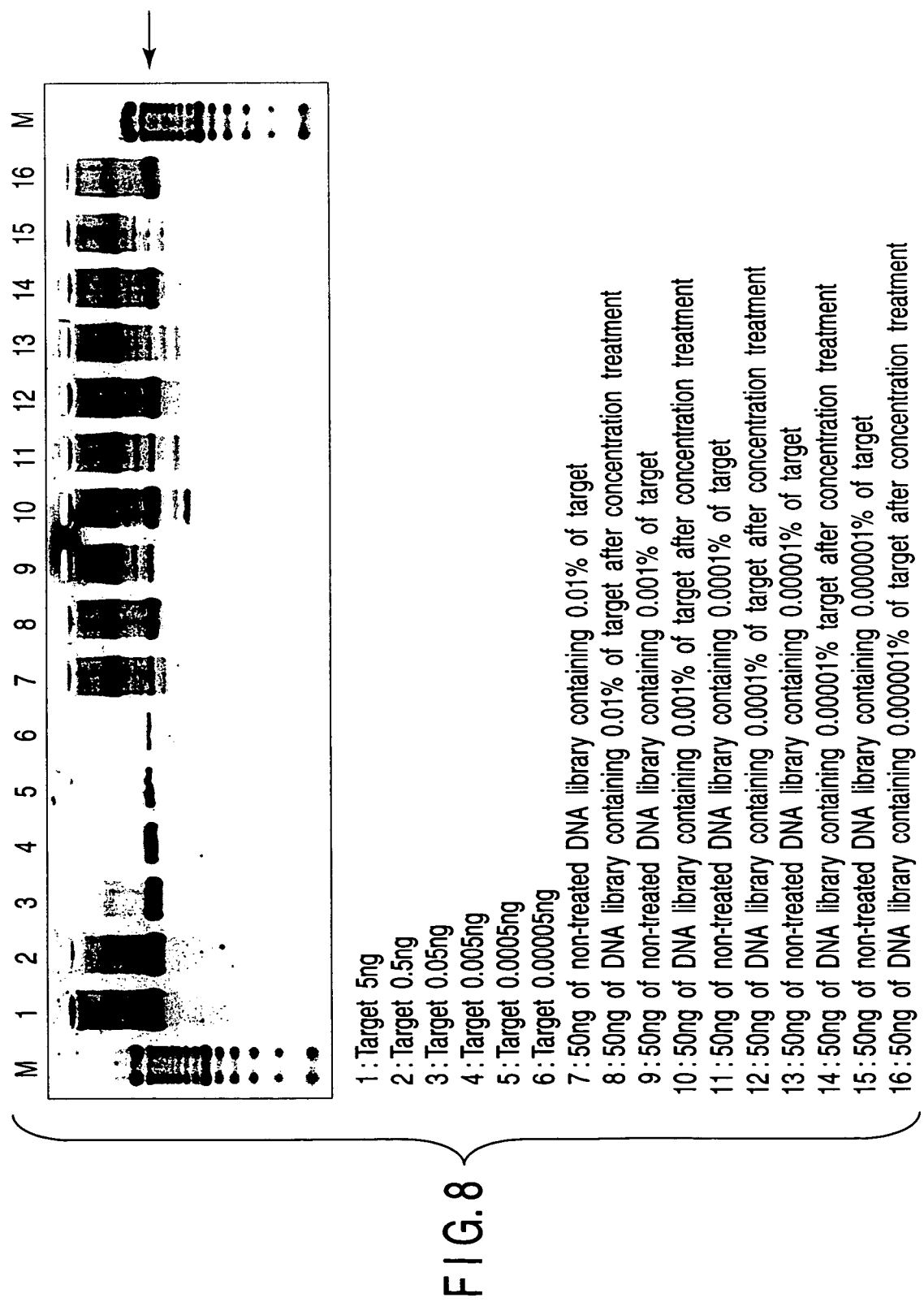

SEQUENCE LISTING

<160> NUMBER OF SEQ ID NOS: 8

<210> SEQ ID NO 1
<211> LENGTH: 25
<212> TYPE: DNA
<213> ORGANISM: Artificial
<220> FEATURE:
<223> OTHER INFORMATION: oligo DNA

<400> SEQUENCE: 1
gggatccact agttctagag cggcc                                    25

<210> SEQ ID NO 2
<211> LENGTH: 29
<212> TYPE: DNA
<213> ORGANISM: Artificial
<220> FEATURE:
<223> OTHER INFORMATION: oligo DNA

<400> SEQUENCE: 2
ccgggggatc cactagttct agagcggcc                                29

<210> SEQ ID NO 3
<211> LENGTH: 40

```
<212> TYPE: DNA
<213> ORGANISM: Artificial
<220> FEATURE:
<223> OTHER INFORMATION: oligo DNA

<400> SEQUENCE: 3
attcctgcag cccgggggat ccactagttc tagagcggcc                              40

<210> SEQ ID NO 4
<211> LENGTH: 60
<212> TYPE: DNA
<213> ORGANISM: Artificial
<220> FEATURE:
<223> OTHER INFORMATION: oligo DNA

<400> SEQUENCE: 4
atcgataagc ttgatatcga attcctgcag cccgggggat ccactagttc tagagcggcc        60

<210> SEQ ID NO 5
<211> LENGTH: 20
<212> TYPE: DNA
<213> ORGANISM: Artificial
<220> FEATURE:
<223> OTHER INFORMATION: oligo DNA

<400> SEQUENCE: 5
gaacccaaag cccacaccag                                                   20

<210> SEQ ID NO 6
<211> LENGTH: 27
<212> TYPE: DNA
<213> ORGANISM: Artificial
<220> FEATURE:
<223> OTHER INFORMATION: oligo DNA

<400> SEQUENCE: 6
gggaacaaaa gctggagctc caccgag                                           27

<210> SEQ ID NO 7
<211> LENGTH: 20
<212> TYPE: DNA
<213> ORGANISM: Artificial
<220> FEATURE:
<223> OTHER INFORMATION: oligo DNA

<400> SEQUENCE: 7
caggactcca gcaaagcact                                                   20

<210> SEQ ID NO 8
<211> LENGTH: 24
<212> TYPE: DNA
<213> ORGANISM: Artificial
<220> FEATURE:
<223> OTHER INFORMATION: oligo DNA

<400> SEQUENCE: 8
cgccagggtt ttcccagtca cgac                                              24
```

PARTIAL HOMOLOGOUS RECOMBINATION OF DNA CHAIN

CROSS-REFERENCE TO RELATED APPLICATIONS

This application is based upon and claims the benefit of priority from prior Japanese Patent Application No. 2003-068176, filed Mar. 13, 2003, the entire contents of which are incorporated herein by reference.

BACKGROUND OF THE INVENTION

1. Field of the Invention

The present invention relates to a method of removing a gene and method of obtaining the gene by partial homologous recombination of a DNA chain.

2. Description of the Related Art

A DNA library, in particular, a cDNA library, is an extremely useful tool for cloning a gene. Numerous genes have been so far cloned from a cDNA library. A cloned gene is used for determining not only the sequences of the gene but also the amino acid sequence of a protein encoded by the gene, and also used for producing the protein in bacterial and yeast cells in a large amount.

However, cDNAs easily cloned from a cDNA library are limited to those prepared from mRNA (used as a template) expressing in a large amount in cells. Since numerous genes have been now cloned, almost all of the easy-to-clone cDNAs have been cloned. Therefore, it has become difficult to efficiently clone a novel cDNA.

To efficiently clone a novel cDNA from a cDNA library, it is necessary to remove cDNAs already cloned from the cDNA library. To attain this purpose, the following techniques have been established.

As a basic method for removing a cDNA, subtractive hybridization is known.

In the method, mRNAs are prepared from both cells (or tissues) expressing and not expressing a desired gene. Then, cDNAs are synthesized from one of the mRNAs and hybridized with the other mRNAs; with the result that the common cDNAs in both cells are exclusively removed. In this way, a gene expressed specifically in certain tissues and cells can be condensed and isolated.

As the subtractive hybridization, subtractive hybridization performed on membrane and subtractive hybridization using a hydroxyapatite column are known (Hedrick S M et al., Isolation of cDNA clones encoding T cell-specific membrane-associated proteins, "Nature", (UK), 1984, Vol. 5955, p. 149–53; and Bonaldo MF et al., Normalization and subtraction: two approaches to facilitate gene discovery, "Genome Res", (USA), 1966, Vol. 9, p 791–806).

However, the on-membrane subtractive hybridization has a problem in that it is difficult to treat many colonies at a time and therefore it is not suitable for reconstructing the entire library. In addition, false positive or false negative error signals are frequently observed. The analysis takes a long time.

On the other hand, the subtractive hybridization using a hydroxyapatite column has a problem. In the case of a cDNA library containing relative long sequences exceeding 3 kb, the possibility of nonspecific hybridization becomes high. Therefore, this subtractive hybridization has been applied only to cDNA library constructed by relatively short cDNAs within about 0.4 to 2.5 kb. A long sequence has a high possibility of containing functionally important genes that encode multifunctional proteins and complex structure proteins. Therefore, the feature of this method which is not applicable to a library containing long sequences is a serious disadvantage of this method. This method has another disadvantage: even though cDNAs are short, the cDNAs derived from the same gene and have the same 3' terminal and 5' terminal, but differ in the middle sequence, cannot be distinguished from each other by this method.

Besides these, there is another method frequently used to achieve the same purpose, a differential display method is known (Liang P et al., Analysis of altered gene expression by differential display, "Method Enzymol", (USA), 1995, vol. 254, p. 304–21). Furthermore, subtractive hybridization method using PCR, which improves the differential display method is also known (Diatchenko L et al., Suppression subtractive hybridization: a versatile method for identifying differentially expressed genes, "Methods Enzymol", (USA), 1999, Vol. 303, p. 349–80).

However, these methods mentioned above have disadvantages: unless the expression levels of genes significantly differ, electrophoretic patterns show no difference. In addition, false positive and false negative error signals are frequently observed. Furthermore, since clones are not directly obtained, they must be cloned by any means based on PCR products thereof.

On the other hand, as a conventional technique for obtaining a desired gene from a gene library, the on-membrane hybridization is known (Hedrick S M et al., Isolation of cDNA clones encoding T cell-specific membrane-associated proteins, "Nature", (UK), 1984, Vol. 5955, p. 149–53).

In this method, colonies or plaques appearing on a plate where Escherichia coli (used as a host) are grown are transferred onto a membrane filter. A detection probe is then hybridized to the membrane filter. It is presumed that the colonies or plaques expressing signals may contain a desired gene fragment. Therefore, the colonies or plaque are isolated and cultured, thereby obtaining the desired gene fragment.

However, in this technique, it is not suitable for obtaining a rare gene, since it is difficult to treat a large number of colonies at a time. Furthermore, false positive and false negative error signals are frequently observed, so that analysis requires a long time.

Furthermore, a method using liquid phase hybridization is known (Invitrogen Instruction Manual, Gene Trapper cDNA Positive Selection System, Cat. No. 10356-020).

In this method, a library is constructed by using a vector having an M13 replication origin. This is converted into a library containing circular single-stranded gene fragments within *Escherichia coli* (*E. coli*) or in vitro. The obtained library is then subjected to hybridization with a labeled probe in a liquid phase, and then, hybridized DNA is isolated by binding the label onto a solid phase via a substance recognizing the label. After it is recovered from the solid phase, the hybridized DNA is converted into a double stranded DNA, which is then introduced into *E. coli* to transform it. In this manner, a desired gene can be obtained.

However, this method has a problem: when no less than 70% of sequences of DNA are homologous to other DNA, the probes non-specifically hybridize to homologous DNA. Therefore, the probe cannot be designed so as to bind to an desired portion.

For other methods to obtain a desired gene from a library, a cloning method using a RecA protein is disclosed (National Patent Publication No. 6-500926).

In this method, first, a triple-stranded DNA is formed with a labeled probe in a liquid phase, and then isolated by binding it onto a solid phase via a substance specifically recognizing the label. The DNA is recovered from the solid phase and thereafter introduced into *E. coli* to transform it. In this manner, a desired gene can be obtained.

However, this method also has a problem. A circular double stranded DNA is only used in the reaction. Therefore, the specificity and efficiency are not always high.

Furthermore, cloning in which a DNA extension reaction is inhibited by a triple-stranded structure is disclosed (Japanese Patent Application KOKAI publication No. 11-206381).

In this method, a library gene is cleaved with a restriction enzyme and a triple-stranded structure is formed at a cleaved site. A triple-stranded structure will be formed in a clone containing a desired gene fragment. Consequently, the clone having a triple-stranded structure formed therein will no longer used as a substrate for a DNA polymerase extension reaction. Therefore, other clones will be only extended. After the reaction, the triple-stranded chain is dissociated and DNA is re-annealed. In this manner, a desired clone can be obtained.

However, this method has a problem: as a degree of specificity increases, the efficiency is decreased. In other words, as the efficiency increases, a degree of specificity decreases.

The present inventors have already disclosed a method of constructing a DNA library having an increased content of a desired gene by using a RecA protein; however, this method fails to use a linear DNA library and thus a further improvement has been desired (Japanese Patent Application KOKAI publication No. 2001-346576).

BRIEF SUMMARY OF THE INVENTION

The present invention has been carried out to overcome the above problems. The present invention is intended to provide a method preparing a DNA library, in which a desired DNA is specifically condensed or removed therefrom, thereby directly obtaining a clone of the desired DNA.

According to the first aspect of the present invention, there is provided a method of constructing a DNA library having an increased content of a first dsDNA by removing a second dsDNA, which is different from the first dsDNA, from a DNA library containing the first dsDNA whose content is to be increased and the second ds DNA, comprising:

(1) adding a third ss nucleic acid, which contains a homologous sequence to a 3' terminal portion of a first strand of the second dsDNA and whose 3' terminal has a different sequence from that of the second dsDNA; and a RecA protein to the DNA library, and leading to homologous recombination between the 3' terminal portion of the first strand of the second dsDNA with the third ss nucleic acid to form a triple stranded portion consisting of the first strand of the second dsDNA, the third ss nucleic acid, and a second strand of the second dsDNA, at the 3' terminal portion of the second dsDNA;

(2) adding Exonuclease I to the DNA library containing a homologous recombinant (triple stranded portion) to digest the first strand of the second dsDNA of the triple stranded portion;

(3) ligating a DNA fragment to circularize the first dsDNA; and (4) removing linear DNA not reacted in the ligation treatment of (3), thereby constructing the DNA library having an increased content of the first dsDNA.

According to a second aspect of the present invention, there is provided a method of constructing a DNA library having an increased content of a first dsDNA by condensing the first dsDNA from a DNA library containing the first dsDNA whose content is to be increased, comprising:

(1) mixing a third ss nucleic acid which contains a homologous sequence to a 3' terminal portion of a first strand of the first dsDNA and contains a sequence capable of providing a restriction site at the 3' terminal portion thereof, and a fourth ss nucleic acid which contains a sequence capable of hybridizing to the 3' terminal portion of the third ss nucleic acid and forming the restriction site at the hybridized portion with the third ss nucleic acid and a label, and hybridizing the 3' terminal portion of the third ss nucleic acid and the fourth ss nucleic acid to form a fifth nucleic acid to forming a restriction site at the double stranded portion of the fifth nucleic acid;

(2) adding a RecA protein and the fifth nucleic acid obtained in the (1) to the DNA library and leading to homologous recombination between a part of the first dsDNA and a portion of the third ss nucleic acid of the fifth nucleic acid to form a triple stranded portion formed of a first strand of the first dsDNA, the portion of the third ss nucleic acid, and a second strand of the first dsDNA, the 3' terminal of the fourth nucleic acid of the fifth nucleic acid flanked by the 5' terminal of the second strand of the first dsDNA;

(3) adding Exonuclease I to the DNA library obtained in the (2) to digest the first strand of the first dsDNA of the triple stranded portion;

(4) recovering a complex containing the fourth ss nucleic acid from the DNA library via the label;

(5) cleaving the restriction site of the complex recovered in the (4) by an appropriate restriction enzyme;

(6) ligating a DNA fragment cleaved in the (5) to circularize the first dsDNA; and (7) removing a linear DNA not reacted in the (6), thereby constructing the DNA library having an increased content of the first dsDNA.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3 is a diagram showing the fundamental principle of a method of condensing a gene according to the present invention;

NXF3c4F: SEQ ID NO. 10
NXF3c4R: SEQ ID NO. 11
NXF3c7F: SEQ ID NO. 12
NXF3c7R: SEQ ID NO. 13
NXF3c14F: SEQ ID NO. 14
NXF3c14R: SEQ ID NO. 15
as20F: SEQ ID NO. 16
as20R: SEQ ID NO. 17
KIAA785F: SEQ ID NO. 18
KIAA785R: SEQ ID NO. 19
KIAA796F: SEQ ID NO. 20
KIAA796R: SEQ ID NO. 21; and FIG. 8 is electrophoretic analysis pattern obtained in the case where a rare gene is condensed.

DETAILED DESCRIPTION OF THE INVENTION

The present inventors found that when a triple-stranded structure is formed at a terminal end region of a target nucleic acid via a RecA protein, the triple-stranded structure can be maintained after the RecA protein is removed from the triple-stranded structure. Based on this finding, the present invention has been achieved. As described, the fact that a triple-stranded structure is formed via a RecA protein and the RecA protein itself are already known.

Figure 1:
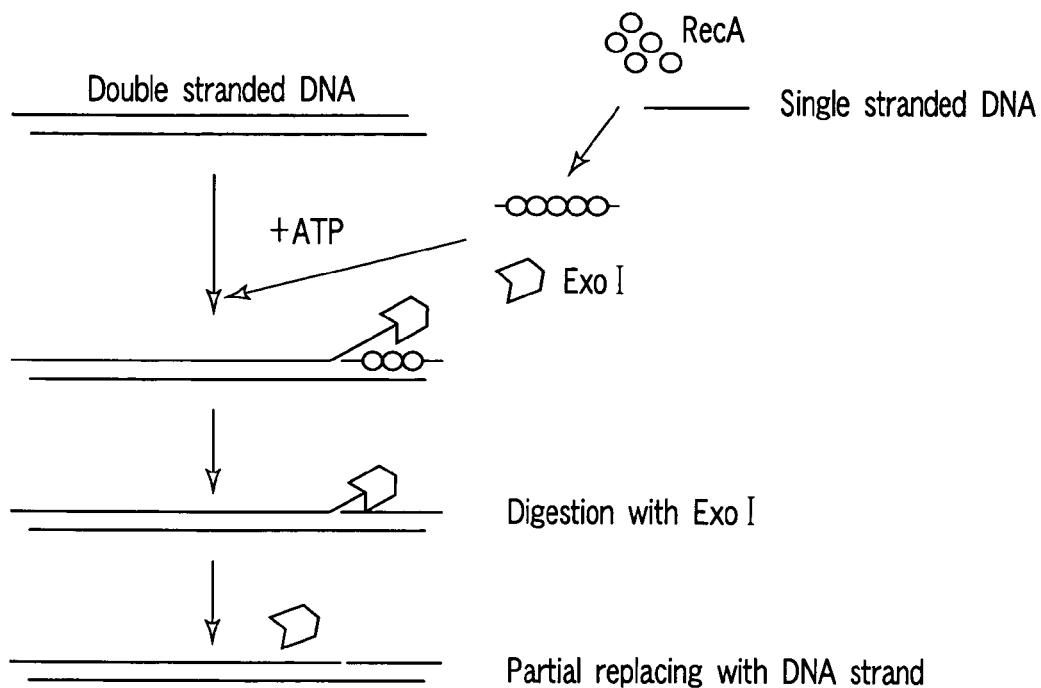
FIG. 1 is a schematic diagram showing an operational mechanism how to exchange part of DNA chain of the present invention.

Referring now to FIG. 1, explanation will be made on a RecA protein used in a method of the present invention and an mechanism of the RecA protein.

It is known that RecA proteins are involved in homologous recombination, DNA repair, and expression of an SOS gene of *E. coli*. *E. coli* RecA protein and λ-phage RecA protein are well known among the RecA proteins. However, a proteins analogous to *E. coli* RecA protein in structure and function are known to widely distribute in many organisms other than *E. coli* and generally called analogous RecA proteins.

As shown in FIG. 1, first, a RecA protein binds to a single stranded DNA (RecA/single stranded DNA filament), and then, mediates the formation of a triplex by paring the single stranded DNA with double stranded DNA. Furthermore, the RecA protein, after a homologous DNA sequence is found, catalyzes a DNA strand exchange reaction in the presence of ATP. After the DNA strand exchange reaction, a double stranded hybrid DNA in which the single DNA strand is incorporated, and a single stranded DNA dissociated from the original double stranded DNA are formed. When the single stranded DNA is shorter than the original double stranded DNA, an exchange reaction occur only at part of the original double stranded DNA. When the single stranded DNA to be replaced has a different terminal sequence from that of the original double stranded DNA, it results in a double-stranded hybrid DNA having different terminal sequence.

As described above, RecA protein does not bind a single-stranded nucleic acid randomly to a double-stranded nucleic acid, but to a homologous region located in either strand of a double-stranded DNA. As used herein, the phrase that two nucleic acids are "homologous" means that they are equivalent or similar enough to allow formation of specific triplex structure via RecA protein. As used herein, the term "simi-lar" refers to, for example, at least 50% or more, preferably 80% or more, more preferably 90% or more, and even more preferably 95% or more identity between the two nucleic acids.

The present invention is a method of removing a defined DNA from a DNA library utilizing the formation of triplex structure DNA by the binding of a single-stranded DNA to a homologous double-stranded DNA via RecA protein.

As used herein, the term "RecA protein" means a protein having an ability to bind a single-stranded nucleic acid to any region in one strand of a double-stranded nucleic acid that is homologous to the single-stranded nucleic acid and mediate formation of the triplex structure in the region.

In the term "RecA protein" are therefore included the RecA-like protein as well as RecA proteins derived from *E. Coli* and lambda phage. As described above, in the present method, the RecA-like protein can be used so long as it has a function that promotes coupling of homologous DNAs and catalyze the formation of a triplexed DNA.

Preferable RecA protein used for the invention is that derived from *E. Coli*.

The term "DNA library" means a group of various DNA fragments and is generally used herein as a general term referring both to a gene library and a cDNA library. The "gene library" means a panel of whole DNA fragments in a single species contained in phages or cosmids, and is equivalent to a "Genomic DNA library". The "cDNA library" means a panel of various cDNA species produced by inserting, into vectors, complementary DNAs (hereinafter referred to as cDNAs) prepared from mRNAs derived from a given tissue or a cell. The DNA fragments may not be circularized by being incorporated into phages, cosmids, or plasmids, thus the library may consist only of the DNA fragments. The DNA library may contain any kinds, for example two kinds of the DNA fragments.

As used herein, the terms, "double stranded DNA", "double stranded RNA", "single stranded DNA", and "single stranded RNA" will be simply referred to as "dsDNA", "dsRNA", "ssDNA", and "ssRNA", respectively. The term, "single stranded nucleic acid" refers to a "single stranded DNA" or a "single stranded RNA" which will be referred to as a "ss nucleic acid".

A method of the present invention will be described below.

According to a first aspect of the present invention, there is provided a method of constructing a DNA library having an increased content of a desired nucleic acid by removing a specific DNA from a DNA library by use of a RecA protein.

In the (1) of the method of the present invention, a ss nucleic acid (hereinafter called "ss nucleic acid 3" for convenience sake) is prepared so as contain a homologous sequence to the 3' terminal portion of one (first strand) of the two strands of dsDNA (hereinafter called a "dsDNA 2") which is desired to remove from a DNA library. The sequence of the 3'-terminal of the ss nucleic acid 3 herein is different from that of the dsDNA 2.

The term "3' terminal portion" used herein refers to a nucleic acid sequence near the 3' terminal; more specifically, includes from the 3' terminal to at least 10 to 40th base, preferably to 60th base, more preferably to 80th base, and most preferably to 100th base or more.

Any nucleic acid may be used as the ss nucleic acid 3 as long as it includes a homologous sequence to the 3' terminal portion of one (first strand) of the strands of the dsDNA 2 to be removed. Therefore, the ss nucleic acid 3 may include other sequences (non-homologous sequence) other than the homologous sequence to the 3' terminal portion of the dsDNA 2. The non-homologous sequence is preferably positioned at the 3' terminal portion of the ss nucleic acid 3. One of the two strands of the dsDNA 2 is defined as a "first strand" above; the other strand is defined as a "second strand".

On the other hand, the ss nucleic acid 3 must not have the same 3' terminal sequence as that of the dsDNA 2. More specifically, the 3' terminal sequence of the dsDNA 2 must have one or more deleted or addicted bases. Thereby, it is possible to prevent circularization of DNA in the subsequent treatment for ligation.

Preparation of the ss nucleic acid 3 containing a homologous sequence to the first strand of the dsDNA 2 may be performed in any method. For example, an in vitro transcription system may be used. In this method, for preparing the ss DNA, a DNA library are transferred into a desired in vitro transcriptable vector (for example, pSPORT1 or pBlueScript SKII), and synthesizing RNA by using an SP6 transcription system (manufactured by Ambion), to synthesize cDNA using reverse transcription using an appropriate primer such as Random primer N6 (manufactured by Takara) and a reverse transcriptase such as SuperScript II RT (manufactured by Invitrogen Corporation).

Finally, a protein is removed using phenol/chloroform to obtain purified ssDNA. If a ssRNA is required, preparation may be performed from the beginning to a synthesizing RNA. The preparation steps for cDNA and RNA as mentioned above will well known to those skilled in the art.

Such ssDNA may be prepared from a dsDNA by another manipulation where the ssDNA is recovered by using a phagemidvector such as pBluescript, pGEM, or puc199 as a phage particle. However, the process for recovering the ssDNA is not limited to these.

Methods of chemical synthesizing DNA and RNA are known to those skilled in the art as shown in the Examples below. These chemical synthetic methods may be used.

Note that the dsDNA 1 (a desired DNA to be maintained) and the dsDNA 2 are carried in plasmids and viral vectors, and thus usually form circular DNA libraries (hereinafter referred to as a "circular DNA library"). When such circular DNAs are used, they must be linearized into linear DNAs, since linear dsDNA must be used in the following treatment. Circular DNA is converted into linear DNA, for example, by cleaving the circular DNA by an appropriate enzyme. In the case where a DNA insert is introduced into a multi-cloning site, the site at which the insert is introduced, may be cleaved by a restriction enzyme. Alternatively, the insert of the circular DNA library may be cleaved and used as the dsDNA 1 and the dsDNA 2. Circular DNA (library) may be cleaved by a restriction enzyme at one or more sites; however, it is preferable to select a restriction enzyme that cleaves circular DNA exclusively at a single site. Those skilled in the art would know how to cleave circular DNA at an appropriate site.

Next, a RecA protein and the ssDNA 3 are added to a solution containing the linear DNA library.

In the ssDNA 3 corresponding to the dsDNA 2, the sequence of its 5' terminal portion is homologous to that of the 3' terminal of the dsDNA 2. Therefore, the ssDNA 3 and a RecA protein are added together, triple stranded DNA is formed (see FIG. 1).

A RecA protein catalyzes homologous recombination in the presence of ATP. Therefore, if ATP is present in a sample, homologous recombination is caused. As a result, homologous recombination is caused between the 3' terminal portion of the first strand of the dsDNA 2 and ss nucleic acid 3 to form a triple stranded portion, which consists of the first strand of the dsDNA 2, the ss nucleic acid 3, the second strand of the dsDNA 2, at the 3' terminal portion of the dsDNA 2 (see FIG. 1).

The homologous recombination reaction is caused in an appropriate buffer under appropriate reaction conditions. More specifically, 20 µl of a solution containing 30 mM Tris-acetic acid (pH 6.9), 1 mM magnesium acetate, 1 mM dithiothreitol, about 100 ng of the ss nucleic acid 3 and 1 µg of RecA protein (manufactured by EPICENTRE) is mixed with 10 µl of a DNA library solution containing 10 mM tris-acetic acid (pH 6.9), 25 mM magnesium acetate, 2 mM dithiothreitol, and the dsDNA 1 and the dsDNA 2, and the resultant solution may be maintained at 37° C. for 15 minutes.

In (2), Exonuclease I is added to the DNA library solution containing a homologous recombinant obtained in the (1) to digest the first strand of the dsDNA 2 of the triple stranded portion (i.e., a strand replaced with the third ssDNA). Exonuclease I is an enzyme degrading a single stranded DNA from the direction of 3' toward 5' terminal. The first strand can be digested by adding Exonuclease I to the DNA library solution under appropriate conditions, or alternatively, by adding another enzyme having the same activity as Exonuclease I.

The digestion reaction by Exonuclease I is carried out by adding, to the aforementioned mixture, a reaction initiation solution (10 µl) containing 20 mM ATP, a 30 mM Tris acetic acid (pH 6.9) and 20 units of Exonuclease I (manufactured by EPICENTRE), 9 mM magnesium acetate, and 2 mM dithiothreitol, and maintaining the reaction mixture at 37° C. for one hour.

Preferably, the reaction mixture thus prepared is subjected to protein removal treatment before the following treatments. Protein may be removed in accordance with a conventional method, for example, by phenol/chloroform treatment.

Next, in (3), the linear dsDNA fragments of a DNA library obtained in the (2) are self-ligated and circularized.

Figure 2:
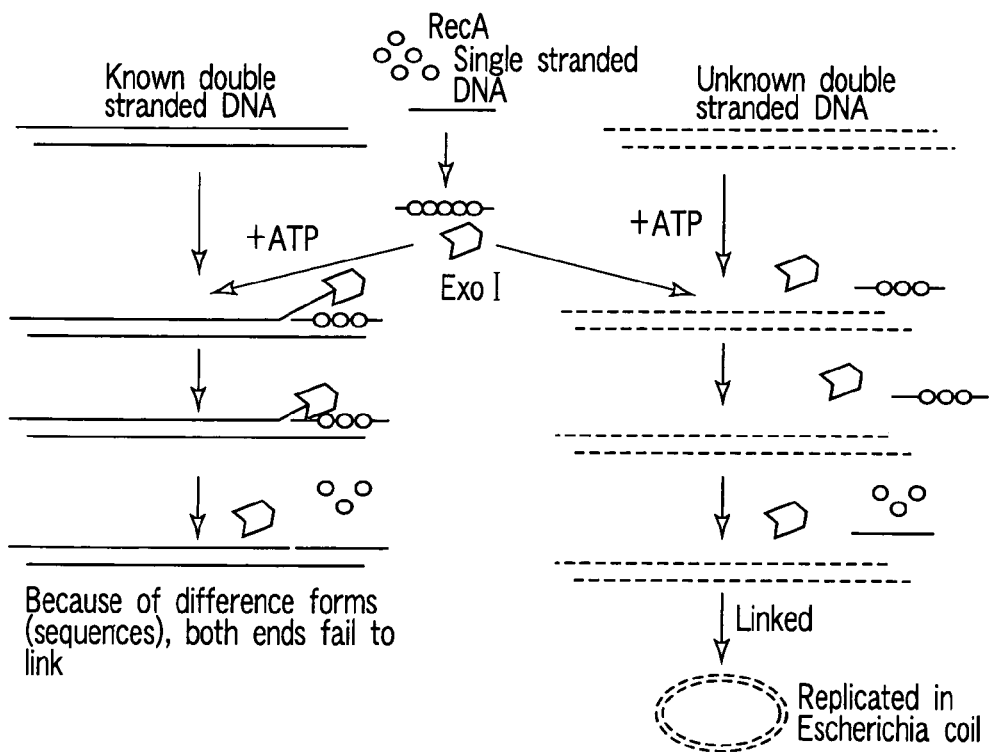
FIG. 2 is a diagram showing the fundamental principle of a method of removing a gene according to the present invention.

If circular DNA fragments contained in the library are cleaved and used as linear DNA fragments in the (1), a self-ligation reaction is caused. At this time, a DNA fragment homologously recombined in the (2) has a different 3' terminal sequence from the original one, and therefore self-ligation does not occur. On the other hand, the dsDNA (dsDNA 1) which has not been homologously recombined is self-ligated to make circular DNA (FIG. 2).

As used herein, the term "self-ligation" means that the 5' terminal of a single linear DNA is ligated with its 3' terminal to form circular DNA.

Furthermore, a linear DNA library such as DNA inserts is used, vectors previously digested with an appropriate restriction enzyme are added to the library to insert linear fragments such as DNA inserts into vectors and circularized. Also in this case, DNA which has been homologously recombined has different 3'-terminal sequence. Therefore, the DNA is not self-ligated. On the other hand, the dsDNA (dsDNA 1) which has not been homologously recombined is self-ligated to form circular DNA.

The ligation above is reacted in accordance with a conventional method. For example, the circular DNA is constructed using T4 DNA Ligase (manufactured Invitrogen Corporation) at 37° C. for 30 minutes. Alternatively, a commercially available ligation kit may be used.

In the present invention, the cycle consisting of treatment of (1) to (4) may be repeated twice or more.

In the (4), the DNA library having an increased content of the dsDNA 1 can be constructed by removing linear DNAs from the DNAs obtained in the previous treatment.

To separate target circular DNAs (the content should be increased) from linear DNAs, agarose electrophoretic separation and a separation using centrifugation in the presence of ethidium bromide may be used. In other case, if a drug-resistant gene is contained in the DNA library, target circular DNA is separated as follows: the DNA is introduced into host cells, to select transformed host cells containing the target circular DNA by the drug treatment. However, a method of separating a target circular DNA is not limited to above.

In the method of the present invention, following the treatment to form a triple stranded structure via a Rec A protein, a RecA protein from the triple stranded structure may be dissociated.

In the method of the present invention, an manipulation for removing a single dsDNA from two dsDNAs has been explained for convenient sake as described in FIG. 2 or above. In a practical manipulation, several tends to several tens of thousands types of dsDNA can be simultaneously or subsequently removed from several thousands to several tens of thousands types of ds DNA.

In the second aspect of the present invention, there is provided a method of constructing a DNA library containing an increased content of a dsDNA 1 by condensing dsDNA 1 from a DNA library containing a dsDNA 1 using a RecA protein.

In the treatment (1) of this method, a ss nucleic acid 3 and a ss nucleic acid 4 are first prepared. In this case, the ss nucleic acid 3 is prepared so as to contain a sequence homologous to the 3' terminal of a first strand of the dsDNA 1 which is to be condensed from the DNA library, and a sequence which can provide a restriction site at the 3' terminal thereof.

In the ss nucleic acid 3, any ss nucleic acid may be used as long as it contains a homologous sequence to the 3' terminal portion of one of the two strands of the dsDNA 1 to be condensed. More specifically, ss nucleic acid 3 may contain a sequence other than the homologous sequence to the 3' terminal portion of the dsDNA 1 and a sequence that can provide a restriction site. One of the strands of the dsDNA 1 is specified as a first strand and the other, a second strand.

On the other hand, the ss nucleic acid 4 is prepared so as to contain a sequence capable of hybridizing with the 3' terminal portion of the ss nucleic acid 3 (that is, a sequence capable of providing a restriction site) and capable of providing a restriction site therein. The 3' terminal of the ss nucleic acid 4 has a sequence adjacent to the 5' terminal of the dsDNA 2 and the ss nucleic acid 4 is labeled.

More specifically, the ss nucleic acid 3 may be designed as follows. The 3' terminal portion of the ss nucleic acid 3 is designed so as to contain a sequence capable of providing an appropriate restriction site when the ss nucleic acid 3 is hybridized with the ss nucleic acid 4. Thereby, the label can be easily cleaved to remove after the ss nucleic acid 3 is recovered from the library in the following treatment.

The sequence capable of providing a restriction site may be cleaved with any restriction enzyme. It is preferable that the cleaved site of the sequence be acceptable for ligation. The restriction site is preferably a multi-cloning site. More specifically, as shown in Example 5, the sequence is designed so as to contain a sequence consisting of 5' terminal—homologous sequence to the dsDNA 2-restriction site—3' terminal.

Although the ssDNA 3 may be prepared in any method as described in the first aspect of the present invention, it can be prepared, for example, by an in vitro transcription system. Also, the ss nucleic acid 3 can be easily prepared by performing reverse transcription using a primer designed so as to contain a desired restriction site. For example, when the multicloning site of the circular DNA library is cleaved and the cleaved sDNA is used as the dsDNA 1, a primer is prepared by using a complementary sequence to the multicloning site as the sequence to be cleaved by a restriction enzyme, and then reverse transcription may be performed. Chemical synthesis may be used, and methods of preparing DNA and RNA by chemical synthesis are known to those skilled in the art.

On the other hand, the ss nucleic acid 4 is designed so that it contain a sequence capable of hybridizing with the 3' terminal portion of the nucleic acid 3 and that the sequence can provide a restriction site at the hybridized portion. The sequence capable of hybridizing with the 3' terminal of the ss nucleic acid 3 is preferably a complementary sequence to the 3' terminal portion of the ss nucleic acid 3. The 3' terminal of the ss nucleic acid 4 is flanked by the 5' terminal of a second strand of the dsDNA 1 when homologous recombination is proceeded in accordance with the following treatment.

Furthermore, the ss nucleic acid 4 is labeled. As the label, any label may be used as long as it can be recovered. For example, biotin is used. The label may be attached to any portion of the ss nucleic acid 4 as long as a nucleic acid 5 can be formed, and preferably labeled with the 5' terminal of the ss nucleic acid 4.

More specifically, the ss nucleic acid 4 is designed so as to contain 5' terminal—(label)—(a sequence capable of hybridizing with the 3' terminal portion of ssDNA 3 (i.e., containing a restriction enzyme cleaving sequence))—3' terminal, wherein-the 3' terminal is flanked by the 5' terminal of dsDNA 2).

The labeled nucleic acid can be prepared by chemical synthesis. For example, a method of chemically synthesizing a biotin-labeled oligonucleotide by using a biotin-labeled nucleotide is known to those skilled in the art. Since such a labeled oligonucleotide is commercially available, it may be used herein.

Next, the ss nucleic acid 3 and the ss nucleic acid 4 are mixed in a solution, inactivated with heat and cooled. In this manner, a hybrid (called nucleic acid 5 herein) is formed between the sequence having a restriction site of the ss nucleic acid 3 and the sequence having a restriction site of the ss nucleic acid 4; and simultaneously, a restriction site is formed at the double stranded portion of the ds nucleic acid 5. More specifically, the hybrid is formed by heating the mixed solution of the ss nucleic acid 3 and the ss nucleic acid 4 to 94° C., followed by cooling it.

In (2), to a solution containing the DNA library, a RecA protein and the nucleic acid 5 (a hybrid between the ss nucleic acid 3 and the ss nucleic acid 4) obtained in the (1) are added (FIG. 3). As a result, homologous recombination is caused between part of the dsDNA 1 and the ss nucleic acid 3 of the nucleic acid 5. The homologous recombination is caused in a buffer under appropriate conditions in the same manner as in the method according to the first aspect. For example, 20 µl of a solution containing 30 mM Tris-acetic acid (pH 6.9), 1 mM magnesium acetate, 1 mM dithiothreitol, 100 ng of nucleic acid 5 (a hybrid between ss nucleic acid 3 and ss nucleic acid 4), and 1 µg of RecA protein (manufactured by EPICENTRE) is mixed with 10 µl of a solution containing 30 mM tris-acetic acid (pH 6.9), 25 mM magnesium acetate, 2 mM dithiothreitol, and 50 ng of a DNA library containing dsDNA 1, and maintained at 37° C. for 15 minutes.

As a result of homologous recombination, a triple stranded portion is formed of the first and the second strands of the dsDNA 1 and the nucleic acid 3. At this time, the 3' terminal of the nucleic acid sequence 4 of the nucleic acid 5 is flanked by the 51 terminal of the second strand of the dsDNA 1.

Subsequently, in (3), Exonuclease I is added to the DNA library obtained in the (2). As a result, the first strand portion of the dsDNA 1 of the formed triple stranded portion is digested (FIG. 3). The digestion with Exonuclease I is performed in the same manner as in the method according to the first aspect (see the (2) of the method of the first aspect).

After the digestion with Exonuclease I, proteins are preferably removed as described above.

Next, in (4), the complex containing teh ss nucleic acid 4 is recovered from the DNA library via the label (FIG. 3). The complex includes the first strand of the nucleic acid 1 (partially digested), the second strand of the nucleic acid 1, the nucleic acid 3 and the nucleic acid 4 (i.e., nucleic acid 5).

The complex is recovered via the label of the ss nucleic acid 4. For example, when teh ss nucleic acid 4 is labeled with biotin, the DNA complex is bonded to streptavidin beads via biotin and recovered. More specifically, streptavidin beads may be added to a solution containing the complex to bind to biotin. The method for recovering the complex may vary depending upon the label to be used. For example, anti-label antibody-immobilized beads may be used.

After recovery, a carrier binded to the complex is preferably washed to remove free nucleic acids (nucleic acids other than the nucleic acid 1 of the DNA library).

In (5), an appropriate restriction enzyme is applied to the complex recovered in the (4) to cleave the nucleic acid 5 at the restriction site. A restriction enzyme capable of cleaving the restriction site of the nucleic acid 5 (a hybrid between the ss nucleic acid 3 and the nucleic acid 4) may be used. More specifically, the enzyme which can cleave the restriction site of the integrated sequence of the ss nucleic acid 3 is used.

According to this treatment, the label recovered in the previous treatment still remains binding to the carrier for recovering a complex. On the other hand, only a DNA complex cleaved at a desired restriction site is removed from the carrier. As a result, a desired nucleic acid portion is exclusively recovered and the separation/purification is not required.

After cleavage with restriction enzyme, it is preferable that protein be removed.

Subsequently, in (6), the DNA cleaved in the (5) is ligated to circularize the dsDNA 1.

Further, in the subsequent treatment, linear DNA is removed. In this manner, a DNA library having an increased content of the dsDNA 1 can be constructed.

Circularization of DNA and removal of linear DNA are performed as described in the first aspect of the present invention. For example, when linear DNA library such as DNA insert is used, insert DNA may be introduced in a desired vector in the same manner as in a conventional cloning method. More specifically, the insert DNA obtained may be introduced in a vector, which has been cleaved at the same restriction site as in the (5).

In a third aspect of the present invention, there is provided a kit for constructing a DNA library having an increased content of desired DNA by the above method.

In accordance with the method of a first aspect, in a kit for constructing a DNA library having an increased content of the dsDNA 1 by removing the dsDNA 2 (different from the dsDNA 1) from the DNA library containing the dsDNA 2 and the dsDNA 1, contains a RecA protein, an appropriate buffer, and Exonuclease I.

In accordance with the method of a second aspect, in a kit for constructing a DNA library having an increased content of dsDNA 1 by condensing dsDNA 1 from the DNA library containing the dsDNA 2 and dsDNA 1, contains a RecA protein, an appropriate buffer, and Exonuclease I.

More specifically, a kit for constructing a DNA library according to a method of the present invention may include a RecA protein, an appropriate buffer, and Exonuclease I in a separate container. More specifically, the kit includes 1 µg of RecA protein and 20 units of Exonuclease I, and it may include further as appropriate buffer, a buffer suitable for a RecA protein activity, and a buffer suitable for Exonuclease I activity as a dose for constructing the DNA library according to the above method. Examples of the appropriate buffer includes a buffer solution containing 30 mM tris-acetic acid (pH 6.9), 1 mM magnesium acetate, 1 mM d dithiothreitol, and a buffer solution containing 30 mM tris-acetic acid (pH 6.9), 9 mM magnesium acetate, and 2 mM dithiothreitol. The RecA protein and Exonuclease I may be respectively dissolved and mixed in the buffer solutions on the reaction. The RecA protein and Exonuclease I may be provided in a dissolved state in an appropriate buffer. For example, the RecA protein may be provided in a mixed state in an appropriate buffer which contains 30 mM tris-acetic acid (pH 6.9), 1 mM magnesium acetate, 1 mM dithiothreitol, and 1 µg of a RecA protein as partial exchange reaction solution I. Exonuclease I may be provided in a mixed state in an appropriate buffer which contains 20 mM ATP, 20 units of Exonuclease I, 30 mM Tris acetic acid (pH 6.9), 9 mM magnesium acetate, and 2 mM dithiothreitol as a reaction initiation solution (10 µl). The kit may further contain substances, such as DNA (e.g., plasmid) required for constructing a DNA library and appropriate restriction enzymes.

Furthermore, the kit for constructing a DNA library according to the method of the second aspect preferably contains a labeled nucleotide (as the fourth ss DNA in the method according to the second aspect) and a carrier capable of recovering the labeled nucleotide. More specifically, the labeled nucleotide is preferably a biotin-labeled nucleotide and the carrier capable of recovering a labeled nucleotide is preferably a streptavidin bead.

The present invention will be explained more specifically by way of Examples.

The figures show specific reactions and structures, which are described to facilitate the understanding of the present invention and the details of them may not always coincide with the description of the specification.

EXAMPLE 1

Removal of Plasmid with No Insert

Partial exchange reaction solution I containing 30 mM Tris acetic acid (pH 6.9), 1 mM magnesium acetate, 1 mM dithiothreitol, vector pBlueScript SKII (+), 100 ng of a sequence specific oligo DNA: 5'-ATCCGATAAAGCT-TGATATCGAATTCCTGCAG CCCGGGGGATCCAC-TAGTTCTAGAGCGGCC-3' (SEQ ID NO: 1), and 1 µg RecA protein (manufactured by EPICENTRE) was prepared.

Partial exchange reaction solution II containing 30 mM Tris acetic acid (pH 6.9), 25 mM magnesium acetate, 2 mM dithiothreitol, and 50 ng of a linear double stranded DNA mixture containing plasmid DNAs with and without an insert and digested with restriction enzyme NotI at a single site was prepared.

Figure 4:
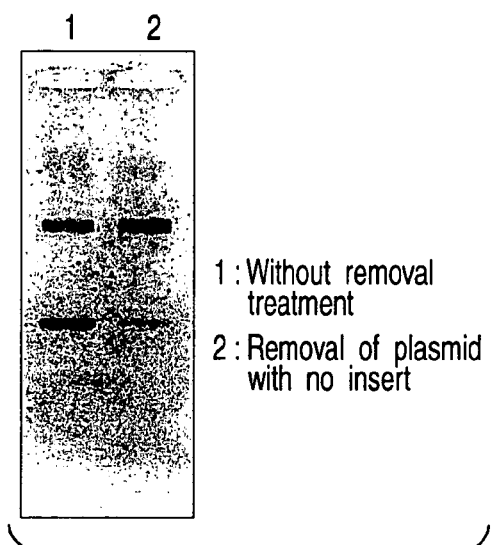
FIG. 4 is an electrophoretic analysis pattern obtained when a plasmid having no insert is removed.

Twenty μl of partial exchange reaction solution I and ten μl of partial exchange reaction solution II were mixed and maintained at 37° C. for 15 minutes. To the resultant solution, 10 μl of a reaction initiation solution containing 20 mM ATP, 30 mM Tris-acetic acid (pH 6.9) containing 20 units of Exonuclease I (manufactured by EPICENTRE), 9 mM magnesium acetate and 2 mM dithiothreitol, was added. After the mixture was allowed to react for one hour at 37° C. and protein was removed, a ligation reaction was performed and the ligation product was introduced into *E. coli* and the plasmid was recovered. As a result, it was found that 99% of vectors were removed (FIG. 4).

EXAMPLE 2

Removal of Plasmid and the Length of Oligonucleotide

Partial exchange reaction solution I containing 30 mM Tris acetic acid (pH 6.9), 1 mM magnesium acetate, 1 mM dithiothreitol, vector pBlueScript SKII (+), 100 ng of each of sequence specific oligo DNA sequences:

| | |
|---|---|
| pBSSN25: 5'-GGGATCCACTAGTTCTAGAGCGGCC-3', | (SEQ ID NO: 2) |
| pBSSN30: 5'-CCGGGGGATCCACTAGTTCTAGAGCGGCC-3', | (SEQ ID NO: 3) |
| pBSSN40: 5'-ATTCCTGCAGCCCGGGGGATCCACTAGTTCTAGAGCGGCC-3', | (SEQ ID NO: 4) |
| pBSSN60: 5'-ATCGATAAGCTTGATATCGAATTCCTGCAGCCCGGGGGATCCACTAGTTCTAGAGCGGCC-3', | (SEQ ID NO: 5) | and 1 μg RecA protein (manufactured EPICENTRE) was prepared.

Partial exchange reaction solution II containing 10 mM Tris acetic acid (pH 6.9), 25 mM magnesium acetate, 2 mM dithiothreitol, and 50 ng of a linear double stranded DNA mixture containing plasmid DNAs with and without an insert and digested with restriction enzyme NotI at a single site was prepared.

Figure 5:
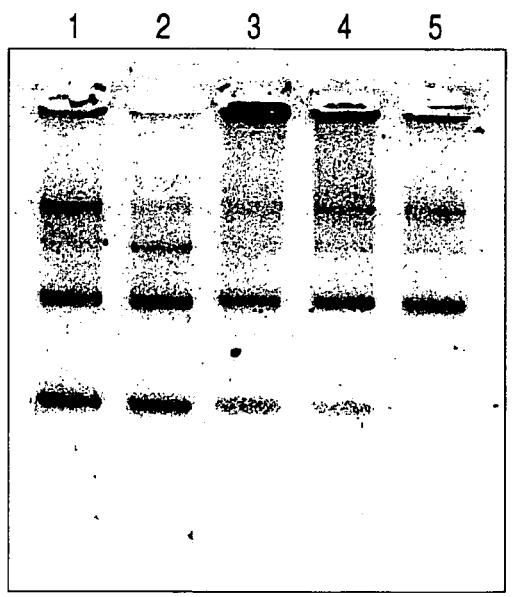
FIG. 5 is an electrophoretic analysis pattern showing the relationship between the removal of a plasmid and the length of oligonucleotide.

Twenty μl of partial exchange reaction solution I and ten μl of partial exchange reaction solution II were mixed and maintained at 37° C. for 15 minutes. To the resultant solution, 10 μl of a reaction initiation solution containing 20 mM ATP, 30 mM Tris-acetic acid (pH 6.9) containing 20 units of Exonuclease I (manufactured by EPICENTRE), 9 mM magnesium acetate, and 2 mM dithiothreitol, was added. After the mixture was allowed to react for one hour at 37° C. and protein was removed, a ligation reaction was performed, the ligation product was introduced into *E. coli,* and the plasmid was recovered. As a result, it was found that a removal ratio of vectors is significantly better in the case of DNA having 40 bases or more (FIG. 5).

EXAMPLE 3

Removal of Vector Using RNA

After a vector, pBLUEScript SK(II), was digested with restriction enzyme NotI, RNA was synthesized in vitro by using a T7 promoter and purified in accordance with a conventional method.

Partial exchange reaction solution I containing 30 mM Tris acetic acid (pH 6.9), 1 mM magnesium acetate, 1 mM dithiothreitol, 100 ng of RNA synthesized in-vitro and 1 μg RecA protein (manufactured EPICENTRE) was prepared.

Partial exchange reaction solution II containing 10 mM Tris acetic acid (pH 6.9), 25 mM magnesium acetate, 2 mM dithiothreitol, and 50 ng of a linear double stranded DNA mixture containing plasmid DNAs with and without an insert and digested with restriction enzyme NotI at a single site was prepared.

Figure 6:
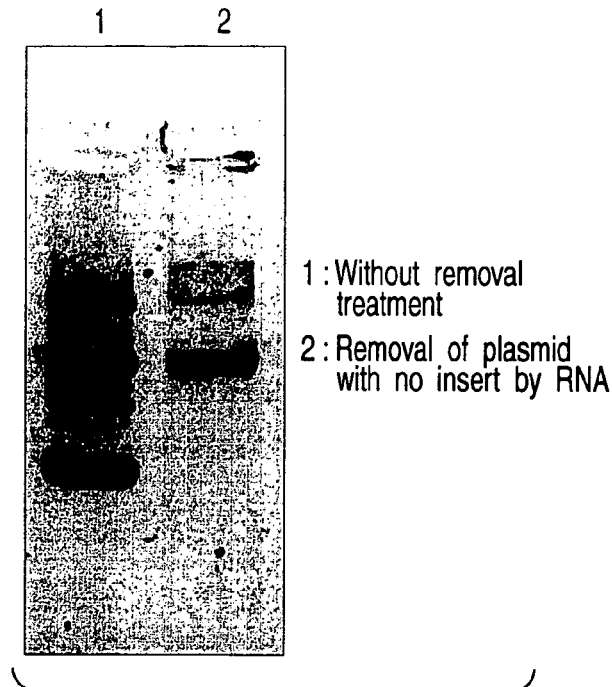
FIG. 6 is an electrophoretic analysis pattern obtained after a vector is removed using RNA.

Twenty μl of partial exchange reaction solution I and ten μl of partial exchange reaction solution II were mixed and maintained at 37° C. for 15 minutes. To the resultant solution, 10 μl of a reaction initiation solution containing 20 mM ATP, 30 mM Tris-acetic acid (pH 6.9) containing 20 units of Exonuclease I (manufactured EPICENTRE), 9 mM magnesium acetate, and 2 mM dithiothreitol was added. After the reaction for one hour at 37° C. and protein was removed, a ligation reaction was performed, the ligation product was introduced into *E. coli,* and a plasmid was recovered. As a result, it was demonstrated that the removal of DNA can be accomplished by use of RNA (FIG. 6).

EXAMPLE 4

Removal of a Large Amount of Clones From a cDNA Library

An inserted gene of a library of a plasmid cDNA derived from the human-brain was digested with restriction enzyme MulI which digested one of the ends of the inserted gene. Using the plasmid as a template, RNA was synthesized by a T3 transcription system (manufactured by Ambion). To 5 μg of the obtained RNA, 6.25 μg of Random primer 6 (manufactured by Takara) was added, inactivated with heat, and immediately cooled on ice. To the resultant mixture, 40 units of an Rnase inhibitor (manufactured by Toyobo Co., Ltd.) and 1 μl of a 5× First strand buffer (manufactured by Invitrogen Corporation) were added. Thereafter, 5 μl of SuperscriptIIRT (manufactured by Invitrogen Corporation) was added to bring the volume of the reaction solution to 20 μl. The reaction mixture was allowed to react at 37° C. for 60 minutes to synthesize cDNA. Subsequently, protein was removed by phenol/chloroform and cDNA was purified.

Partial exchange reaction solution I containing 30 mM Tris acetic acid (pH 6.9), 1 mM magnesium acetate, 1 mM dithiothreitol, 100 ng of reverse transcribed cDNA and 1 μg of a RecA protein (manufacture by EPICENTRE) was prepared.

Partial exchange reaction solution II containing 10 mM Tris acetic acid (pH 6.9), 25 mM magnesium acetate, 2 mM dithiothreitol, and 50 ng of a linear double stranded DNA mixture containing plasmid DNAs with and without an insert and digested with restriction enzyme NotI at a single site was prepared.

Twenty μl of partial exchange reaction solution I and ten μl of partial exchange reaction solution II were mixed and maintained at 37° C. for 15 minutes. To the resultant solution, 10 μl of a reaction initiation solution containing 20 mMATP, 30 mM Tris-acetic acid (pH 6.9) containing 20 units of Exonuclease I (manufactured by EPICENTRE), 9 mM magnesium acetate, and 2 mM dithiothreitol was added. After the mixture was allowed to react for one hour at 37° C. and protein was degraded and purified the DNAs. More specifically, the DNAs was ligated using T4 DNA ligase (manufactured by Invitrogen Corporation) at 37° C. for 30 minutes and the DNA was purified. Thereafter, *E. coli* was transformed, thereby removing a clones which present in an large amount.

Figure 7:
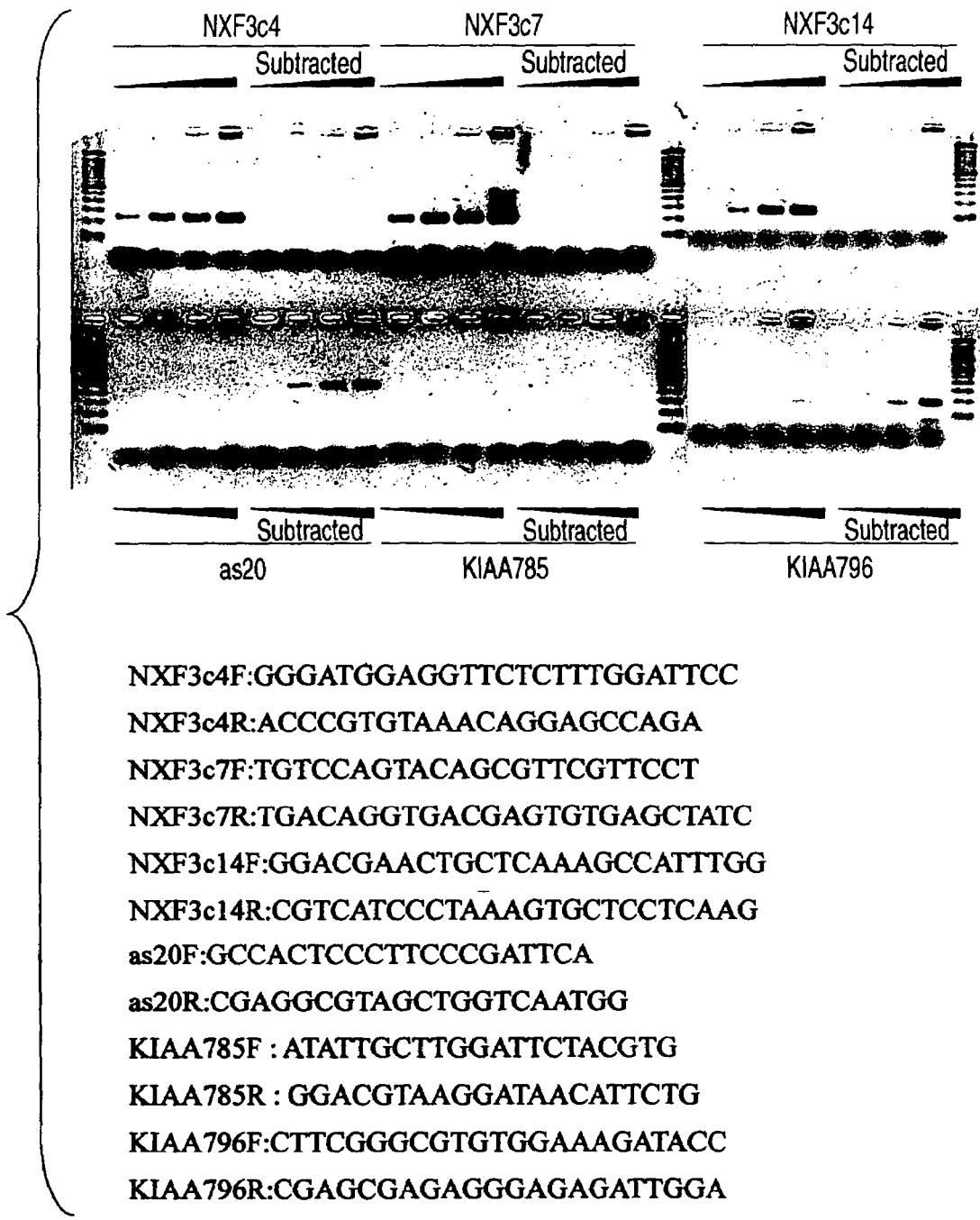
FIG. 7 is an electrophoretic pattern obtained after clones present in a large amount are removed from a cDNA library, the nucleotide sequences shown therein being assigned SEQ ID NOS as follows.

0.1 ng, 1 ng, 10 ng, 100 ng of the library before and after the removal were used as a template, three types of genes present in large amounts and three types of genes present in small amounts were examined by PCR. The genes present in large amounts were removed. It is therefore demonstrated that the genes present in small amounts were relatively condensed (FIG. 7).

EXAMPLE 5

Condensation of Rare Gene

As a model experiment for isolating a rare gene, a plasmid containing a human α-2-macroglobulin gene fragment was condensed.

RNA synthesis was performed in vitro by using a desired clone and a T3 promoter. Using RNA as a template, a single stranded cDNA was synthesized with a reverse transcriptase by using an oligonucleotide C23R600: 5'-GAAC-CCAAAGCCCACACCAG-3' (SEQ ID NO: 6) as a primer. A biotin-labeled oligonucleotide, bio-T3BstX:

5'-GGGAACAAAAGCTGGAGCTCCACCGAG-3' (SEQ ID NO: 7), ranging from near T3 promoter to a multicloning site, was mixed with the cDNA obtained by reverse-transcription, and inactivated with heat and annealed.

Partial exchange reaction solution I containing 30 mM Tris acetic acid (pH 6.9), 1 mM magnesium acetate, 1 mM dithiothreitol, 100 ng of cDNA annealed with a biotin-labeled oligonucleotide, and 1 μg RecA protein (manufactured EPICENTRE) was prepared.

Partial exchange reaction solution II containing 10 mM Tris acetic acid (pH 6.9), 25 mM magnesium acetate, 2 mM dithiothreitol, and 50 ng of a linear double stranded DNA mixture containing plasmid DNAs with and without an insert and digested with restriction enzyme NotI at a single site was prepared.

Twenty μl of partial exchange reaction solution I and ten μl of partial exchange reaction solution II were mixed and maintained at 37° C. for 15 minutes. To the resultant solution, 10 μl of a reaction initiation solution containing 20 mM ATP, 30 mM Tris-acetic acid (pH 6.9) containing 20 units of Exonuclease I (manufactured by EPICENTRE), 9 mM magnesium acetate and 2 mM dithiothreitol was added. After the reaction for one hour at 37° C., protein was removed and a plasmid was isolated by streptavidin beads (manufactured by Dynal). The prasmid is digested with restriction enzyme NotI to recover the plasmid from streptavidin beads. Ligation was performed in the same manner as above and a ligated product was introduced into *E. coli*.

When this is compared to the case where ligation was directly performed without above treatment and a ligated product was introduced into *E. coli*, PCR analysis using C23F198: 5'-CAGGACTCCAGCAAAGCACT-3' (SEQ ID NO: 8) and M13F: 5'-CGCCAGGGTTTTCCCAGTCAC-GAC-3' (SEQ ID NO: 9) demonstrates that a desired nucleic acid was condensed to 1000 folds or more (FIG. 8).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

"Sequence Listing" will be described on the next page and later.

What is claimed is:

1. A method of constructing a DNA library having an increased content of a first dsDNA by removing a second dsDNA, which is different from the first dsDNA, from a DNA library containing the first dsDNA whose content is to be increased and the second dsDNA, comprising:

(1) adding a third ss nucleic acid, which contains a homologous sequence to the DNA library, said third ss nucleic acid containing a sequence that is homologous to a 3' terminal portion of a first strand of the second dsDNA, the homologous sequence being located at a position other than the 3' terminal portion of the third ss nucleic acid, said third ss nucleic acid having a 3' terminal sequence that is different from that of the second dsDNA;

(2) adding a RecA protein to the DNA library, thereby catalyzing homologous recombination between the 3' terminal portion of the first strand of the second dsDNA and the third ss nucleic acid to form a triple stranded portion at the 3' terminal portion of the second dsDNA consisting of the first strand of the second dsDNA, the third ss nucleic acid, and a second strand of the second dsDNA;

(3) adding Exonuclease I to the DNA library containing a homologous recombinant (triple stranded portion) to digest the first strand of the second dsDNA of the triple stranded portion;

(4) ligating a DNA fragment to circularize the first dsDNA; and (5) removing linear DNA not reacted in the ligation treatment of (4), thereby constructing the DNA library having an increased content of the first dsDNA.

2. The method according to claim 1 wherein the DNA library is a circular DNA library, further comprising a treatment for cleaving circular dsDNA prior to step (1).

3. The method according to claim 1, wherein the ligation is self-ligation.

4. A method of constructing a DNA library having an increased content of a first dsDNA, said first dsDNA comprised of a first nucleic acid strand and a second nucleic acid strand, by condensing the first dsDNA from a DNA library containing the first dsDNA whose content is to be increased, comprising:

(1) mixing a third ss nucleic acid which contains a homologous sequence to a 3' terminal portion of a first nucleic acid strand of the first dsDNA and contains a sequence capable of providing a restriction site at the 3' terminal portion thereof, and a fourth ss nucleic acid which contains a sequence capable of hybridizing to the 3' terminal portion of the third ss nucleic acid and forming the restriction site at the hybridized portion with the third ss nucleic acid and a label, and hybridizing the 3' terminal portion of the third ss nucleic acid and the fourth ss nucleic acid to form a fifth nucleic acid to forming a restriction site at the double stranded portion of the fifth nucleic acid;

(2) adding a RecA protein and the fifth nucleic acid obtained in step (1) to the DNA library and leading to homologous recombination between a part of the first dsDNA and a portion of the third ss nucleic acid of the fifth nucleic acid to form a triple stranded portion formed of a first nucleic acid strand of the first dsDNA, the portion of the third ss nucleic acid, and a second nucleic acid strand of the first dsDNA, the 3' terminal of the fourth nucleic acid of the fifth nucleic acid flanked by the 5' terminal of the second nucleic acid strand of the first dsDNA;

(3) adding Exonuclease I to the DNA library obtained in step (2) to digest the first nucleic acid strand of the first dsDNA of the triple stranded portion;

(4) recovering a complex containing the fourth ss nucleic acid from the DNA library via the label;

(5) cleaving the restriction site of the complex recovered in step (4) by an appropriate restriction enzyme;

(6) ligating a DNA fragment cleaved in step (5) to circularize the first dsDNA; and (7) removing a linear DNA not reacted in step (6), thereby constructing the DNA library having an increased content of the first dsDNA.

5. The method according to claim 4 wherein the DNA library is a circular DNA library, further comprising a treatment for cleaving circular dsDNA prior to step (1).

6. The method according to claim 4, wherein the ligation is self-ligation.

* * * * *

UNITED STATES PATENT AND TRADEMARK OFFICE
CERTIFICATE OF CORRECTION

PATENT NO. : 7,220,548 B2
APPLICATION NO. : 10/798750
DATED : May 22, 2007
INVENTOR(S) : K. Kondo et al.

It is certified that error appears in the above-identified patent and that said Letters Patent is hereby corrected as shown below:

| COLUMN | LINE | ERROR |
|---|---|---|
| (56) Pg. 1, col. 2 | Refs. Cited (Other Publs., Item 5) | "Colones" should read --Clones-- |
| 1 | 47 | "T cell-specific" should read --T-cell-specific-- |
| 1 | 61 | "relative long" should read --relatively long-- |
| 1 | 64 | "only to cDNA library" should read --only to a cDNA library-- |
| 2 | 5 | "gene and have" should read --gene and that have-- |
| 2 | 28 | "T cell-specific" should read --T-cell-specific-- |
| 2 | 31 | "Escherichia coli" should read --*Escherichia coli*-- |
| 2 | 37 | "However, in this technique, it is not" should read --However, this technique is not-- |
| 2 | 59 | "an desired" should read --a desired-- |
| 3 | 14-15 | "no longer used as" should read --no longer be used as-- |
| 3 | 43 | "ds DNA," should read --dsDNA,-- |
| 3 | 46 | "a $_3$' terminal" should read --a 3' terminal-- |
| 3 | 47 | "whose $_3$' terminal" should read --whose 3' terminal-- |
| 3 | 63 | "of (3)," should read --of step (3),-- |
| 4 | 12-13 | "to forming a" should read --to form a-- |
| 4 | 16 | "the (1)" should read --step (1)-- |
| 4 | 26 | "the (2)" should read --step (2)-- |
| 4 | 31 | "the (4)" should read --step (4)-- |

UNITED STATES PATENT AND TRADEMARK OFFICE
CERTIFICATE OF CORRECTION

PATENT NO. : 7,220,548 B2
APPLICATION NO. : 10/798750
DATED : May 22, 2007
INVENTOR(S) : K. Kondo et al.

It is certified that error appears in the above-identified patent and that said Letters Patent is hereby corrected as shown below:

| COLUMN | LINE | ERROR |
|---|---|---|
| 4 | 32 | "the (5)" should read --step (5)-- |
| 4 | 34 | "the (6)" should read --step (6)-- |
| 4 | 55 | "how to exchange" should read --for exchanging-- |
| 5 | 19 | after "Fig. 8 is" insert --an-- |
| 5 | 33 | "explanation will be made on" should read --explanation should be made regarding-- |
| 5 | 35 | "an mechanism" should read --a mechanism-- |
| 5 | 55 | "occur" should read --occurs-- |
| 5 | 59 | "having different" should read --having a different-- |
| 6 | 15-16 | "*E. Coli*" should read --*E. coli*-- |
| 6 | 21 | "*E. Coli*" should read --*E. coli*-- |
| 6 | 19 | "catalyze" should read --catalyzes-- |
| 6 | 52 | "so as contain" should read --so as to contain-- |
| 6 | 50 | "the (1)" should read --step (1)-- |
| 6 | 55 | "which is desired" should read --which it is desired-- |
| 7 | 10 | "addicted" should read --additional-- |
| 7 | 15 | "performed in" should read --performed by-- |
| 7 | 17 | "ss DNA" should read --ssDNA-- |
| 7 | 17 | "library are" should read --library is-- |
| 7 | 29 | "will well known" should read --will be well known-- |

UNITED STATES PATENT AND TRADEMARK OFFICE
CERTIFICATE OF CORRECTION

PATENT NO.         : 7,220,548 B2
APPLICATION NO.    : 10/798750
DATED              : May 22, 2007
INVENTOR(S)        : K. Kondo et al.

It is certified that error appears in the above-identified patent and that said Letters Patent is hereby corrected as shown below:

| COLUMN | LINE | ERROR |
|---|---|---|
| 7 | 47 | after "introduced" delete "," |
| 8 | 16 | "In (2)," should read --In step (2),-- |
| 8 | 17 | "recombinant obtained" should read --recombinant DNA obtained-- |
| 8 | 17 | "the (1)" should read --step (1)-- |
| 8 | 21 | "toward 5' terminal" should read --toward the 5' terminal-- |
| 8 | 29 | after "containing" delete "and" |
| 8 | 42 | "the (1)," should read --step (1),-- |
| 8 | 44 | "the (2)" should read --step (2)-- |
| 8 | 52 | after "Furthermore," insert --when-- |
| 8 | 57 | "has different" should read --has a different-- |
| 8 | 63 | after "(manufactured" insert --by-- |
| 8 | 67 | "of (1) to (4)" should read --of steps (1) to (4)-- |
| 9 | 1 | "the (4)" should read --step (4)-- |
| 9 | 2 | before "dsDNA" delete "the" |
| 9 | 7 | "In other" should read --In another-- |
| 9 | 12-13 | "not limited to above" should read --not limited to that detailed above-- |
| 9 | 15 | "Rec A" should read --RecA-- |
| 9 | 18 | "an manipulation" should read --a manipulation-- |

UNITED STATES PATENT AND TRADEMARK OFFICE
CERTIFICATE OF CORRECTION

PATENT NO. : 7,220,548 B2
APPLICATION NO. : 10/798750
DATED : May 22, 2007
INVENTOR(S) : K. Kondo et al.

It is certified that error appears in the above-identified patent and that said Letters Patent is hereby corrected as shown below:

| COLUMN | LINE | ERROR |
|---|---|---|
| 9 | 20 | "for convenient sake" should read --for convenience sake-- |
| 9 | 21 | "several tends" should read --several tens-- |
| 9 | 24 | "ds DNA." should read --dsDNA.-- |
| 9 | 58 | "cleaved to remove" should read --cleaved to be removed-- |
| 9 | 65 | after "consisting of" insert --a-- |
| 10 | 9 | after "prepared" insert --,-- |
| 10 | 10 | after "site" insert --,-- |
| 10 | 16 | "it contain" should read --it contains-- |
| 10 | 17 | "and that" should read --and so that-- |
| 10 | 24 | "is proceeded in" should read --proceeds in-- |
| 10 | 36 | "wherein-the" should read --wherein the-- |
| 10 | 37 | after "dsDNA 2" delete ")" |
| 10 | 54 | "In (2)," should read --In step (2),-- |
| 10 | 56 | "the (1)" should read --step (1)-- |
| 11 | 8 | "51 terminal" should read --5' terminal-- |
| 11 | 10 | "in (3)," should read --in step (3),-- |
| 11 | 11 | "the (2)." should read --step (2).-- |
| 11 | 15 | "the (2)" should read --step (2)-- |
| 11 | 18 | "in (4)," should read --in step (4),-- |

UNITED STATES PATENT AND TRADEMARK OFFICE
CERTIFICATE OF CORRECTION

PATENT NO. : 7,220,548 B2
APPLICATION NO. : 10/798750
DATED : May 22, 2007
INVENTOR(S) : K. Kondo et al.

It is certified that error appears in the above-identified patent and that said Letters Patent is hereby corrected as shown below:

| COLUMN | LINE | ERROR |
|---|---|---|
| 11 | 18 | "the" should read --the-- |
| 11 | 25 | "the" should read --the-- |
| 11 | 33 | "binded to" should read --bound to-- |
| 11 | 36 | "In (5)," should read --In step (5),-- |
| 11 | 37 | "the (4)" should read --step (4)-- |
| 11 | 44 | "binding to" should read --bound to-- |
| 11 | 52 | "in (6)," should read --in step (6),-- |
| 11 | 52 | "the (5)" should read --step (5)-- |
| 11 | 59 | "when linear DNA library" should read --when a linear DNA library-- |
| 11 | 64 | "the (5)." should read --step (5).-- |
| 12 | 21 | "includes" should read --include-- |
| 12 | 21 | "tris-acetic" should read --Tris-acetic-- |
| 12 | 22 | before "dithiothreitol," delete " d " |
| 12 | 23 | "tris-acetic" should read --Tris-acetic-- |
| 12 | 30 | "tris-acetic" should read --Tris-acetic-- |
| 12 | 35 | "Tris acetic" should read --Tris-acetic-- |
| 12 | 67 | "Tris acetic" should read --Tris-acetic-- |
| 13 | 5-6 | "ten µl" should read --10 µl-- |
| 13 | 20 | "Tris acetic" should read --Tris-acetic-- |

UNITED STATES PATENT AND TRADEMARK OFFICE
CERTIFICATE OF CORRECTION

PATENT NO. : 7,220,548 B2
APPLICATION NO. : 10/798750
DATED : May 22, 2007
INVENTOR(S) : K. Kondo et al.

It is certified that error appears in the above-identified patent and that said Letters Patent is hereby corrected as shown below:

| COLUMN | LINE | ERROR |
|---|---|---|
| 13 | 34 | after "(manufactured" insert --by-- |
| 13 | 37 | "Tris acetic" should read --Tris-acetic-- |
| 13 | 65 | "Tris acetic" should read --Tris-acetic-- |
| 13 | 66 | "in-vitro" should read --in vitro-- |
| 13 | 67 | after "(manufactured" insert --by-- |
| 14 | 2 | "Tris acetic" should read --Tris-acetic-- |
| 14 | 7 | "ten µl" should read --10 µl-- |
| 14 | 13 | after "(manufactured" insert --by-- |
| 14 | 35 | "human-brain" should read --human brain-- |
| 14 | 42 | "Rnase" should read --RNase-- |
| 14 | 52 | "Tris acetic" should read --Tris-acetic-- |
| 14 | 57 | "Tris acetic" should read --Tris-acetic-- |
| 14 | 62-63 | "ten µl" should read --10 µl-- |
| 15 | 4 | "DNAs was" should read --DNA was-- |
| 15 | 7 | "a clones" should read --clones-- |
| 15 | 7-8 | "an large" should read --a large-- |
| 15 | 19 | "Gene" should read --Genes-- |
| 15 | 36-37 | after "(manufactured" insert --by-- |
| 16 | 2 | "Tris acetic" should read --Tris-acetic-- |

UNITED STATES PATENT AND TRADEMARK OFFICE
CERTIFICATE OF CORRECTION

PATENT NO. : 7,220,548 B2
APPLICATION NO. : 10/798750
DATED : May 22, 2007
INVENTOR(S) : K. Kondo et al.

It is certified that error appears in the above-identified patent and that said Letters Patent is hereby corrected as shown below:

| COLUMN | LINE | ERROR |
|---|---|---|
| 16 | 7 | "ten µl" should read --10 µl-- |
| 16 | 16 | "prasmid" should read --plasmid-- |
| 16 | 27 | "1000 folds" should read --1000 fold-- |
| 19 (Claim 1, | 13 line 24) | "homologous recombinant" should read --homologous recombinant DNA-- |
| 20 (Claim 4, | 6 line 18) | "to forming" should read --and forming-- |

Signed and Sealed this

Eighteenth Day of December, 2007

JON W. DUDAS
*Director of the United States Patent and Trademark Office*